United States Patent [19]

Khoury

[11] 4,170,232
[45] Oct. 9, 1979

[54] TRACHEO-BRONCHIAL SAMPLER DEVICE

[76] Inventor: Francis E. Khoury, 63 St. Leonards Rd., Hove, Sussex, England

[21] Appl. No.: 824,625

[22] Filed: Aug. 15, 1977

[30] Foreign Application Priority Data

Aug. 26, 1976 [GB] United Kingdom ............... 35642/76

[51] Int. Cl.² ........................................... A61M 25/00
[52] U.S. Cl. ............................. 128/351; 128/DIG. 26
[58] Field of Search ..................... 128/351, 248–250, 128/214.4, 240, 241, DIG. 16, DIG. 26

[56] References Cited

U.S. PATENT DOCUMENTS

| 3,088,466 | 5/1963 | Nichols | 128/351 |
| 3,527,216 | 9/1970 | Snyder | 128/221 X |
| 3,878,835 | 4/1975 | Utsugi | 128/214.4 X |
| 4,054,135 | 10/1977 | Berman | 128/351 X |
| 4,069,814 | 1/1978 | Clemens | 128/240 X |

Primary Examiner—Stephen C. Pellegrino
Attorney, Agent, or Firm—Brisebois & Kruger

[57] ABSTRACT

A tracheo-bronchial sampler device comprises a tubular member insertable into a chest tube and defining a passage through which a sampling catheter can be passed when the chest tube is inserted into the trachea of a patient, means are provided for spacing the passage of said tubular member away from the inner wall of said chest tube, as well as stop means for preventing the insertion of the tubular member through the chest tube beyond a predetermined point. The device enables a sample to be obtained from the desired tracheal region without undesired contamination as the sampling catheter is inserted into the patient.

4 Claims, 6 Drawing Figures

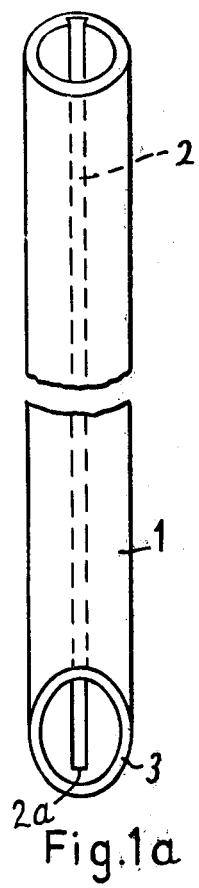
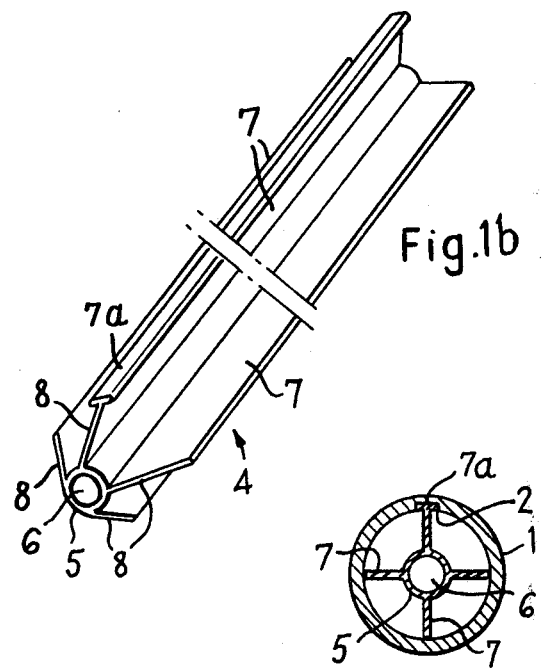
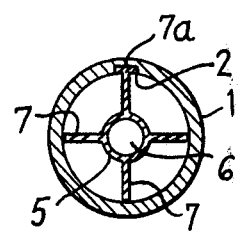
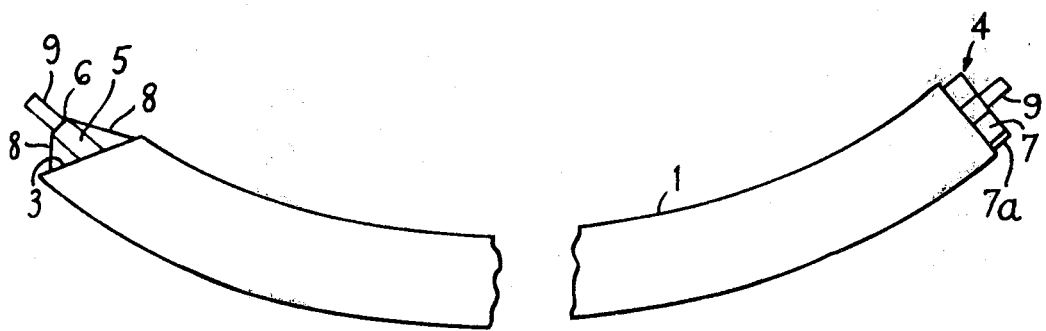

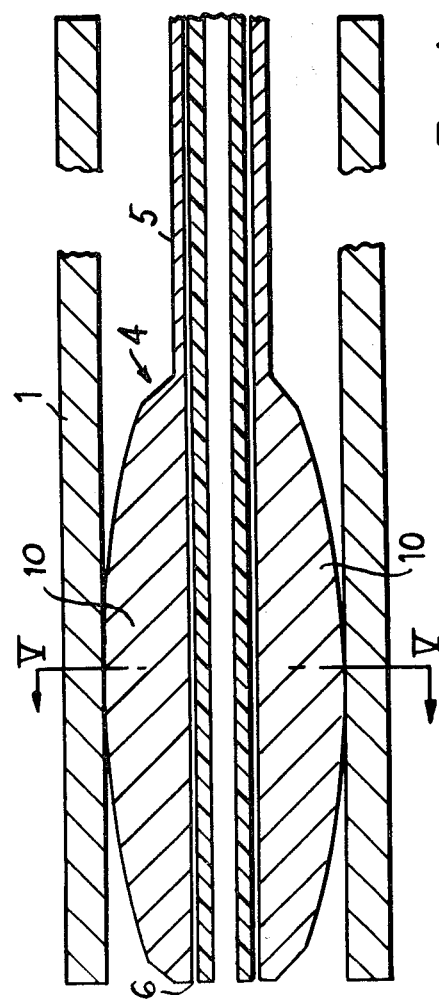
Fig.4
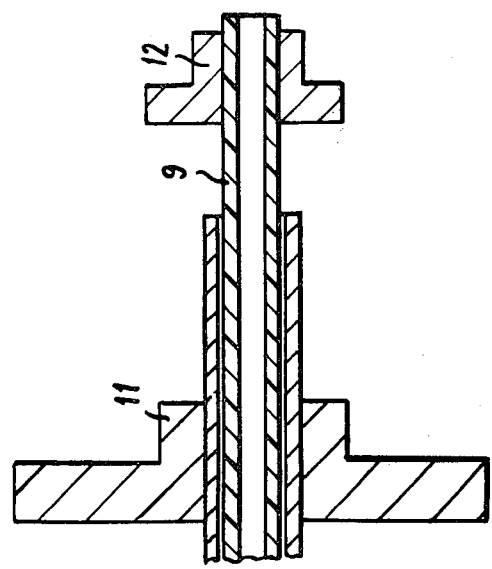
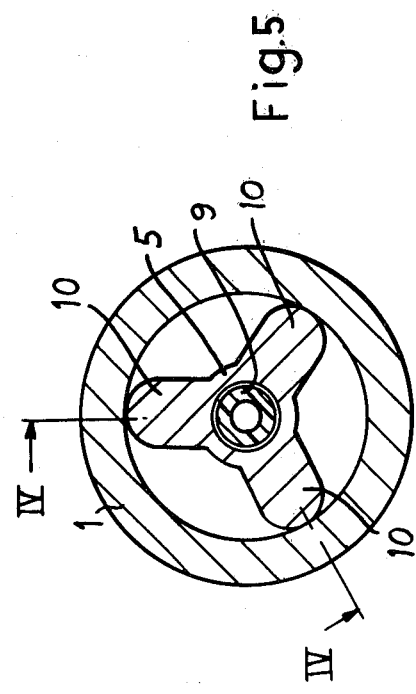
Fig.5

TRACHEO-BRONCHIAL SAMPLER DEVICE

The present invention relates to a tracheobronchial sampler device.

According to the invention, a tracheobronchial sampler device comprises an outer chest tube capable of insertion into the trachea of a patient, a tubular member insertable in said chest tube and defining a passage through which a sampling catheter can be passed into the trachea, means for spacing the passage of said tubular member away from the inner wall of said chest tube and stop means for preventing the insertion of the tubular member through the chest tube beyond a predetermined point.

Preferably, all of the components of the sampler device are made from plastics material.

Advantageously, the tracheal end of the chest tube is oblique or bevelled and the tube which is flexible, may have a curved initial form to facilitate insertion into the trachea of a patient.

In a preferred embodiment, the tubular member is provided with a plurality of longitudinal outwardly projecting webs which are engageable with the inner wall of the chest tube and serve to hold the passage in the tubular member spaced away from the inner wall of the chest tube. In one embodiment, the latter may be provided with a longitudinal groove in its inner wall which slidably receives the outer edge of one of the webs as the tubular member is passed into the chest tube, the tracheal end of the groove being closed to define a stop which is engaged by the web to limit the movement of the tubular member into the chest tube. The tracheal ends of the webs are preferably cutback or bevelled.

The tracheal end of the passage may be normally closed by a thin membrane which is pierced by the sampling catheter as it passes out of the tracheal end of the passage.

According to another embodiment, the tubular member is again provided with a plurality of longitudinal outwardly projecting webs which extend only part-way along the tubular member and which are engageable with the inner wall of the chest tube which has a smooth internal configuration. The stop means is formed by an apertured member which is a frictional fit on the non-webbed part of the tubular member and which includes a region which abuts against the outer end of the chest tube to limit the movement of the tubular member into the chest tube. The sampling catheter may also be provided with a similar stop member which is a frictional fit thereon and which includes a region which abuts against the outer end of the tubular member to limit the amount by which the catheter enters the trachea, when the sampling device is in use.

The invention will now be further described by way of example with reference to the accompanying drawings, in which:

FIGS. 1a and 1b show respectively an embodiment of chest tube and tubular member;

FIG. 2 is a cross-section through the sampler device showing the tubular member inserted in the chest tube, FIG. 3 is a perspective view of the sampler device including a catheter, FIG. 4 is a cross-sectional view on a larger scale of a further embodiment of sampler device, taken on the line IV—IV in FIG. 5, and FIG. 5 is a cross-section on the line V—V in FIG. 4.

Referring to FIGS. 1a, 1b and 2, a tracheobronchial sampler device comprises a flexible chest tube or Magill tube 1 made of a plastics material provided with a longitudinal groove 2 on its inner wall. The tracheal end 3 of this tube is oblique and the adjacent end 2a of the groove is closed.

The tubular member 4, also of a plastics material, comprises a central cylindrical portion 5 defining a passage 6 and has four outwardly projecting webs 7 extending throughout its length and equally spaced around its periphery. One of the webs is provided with a rib 7a along its outer edge which engages in the groove 2 in the chest tube 1, when the tubular member 4 is inserted therein, as can be seen from FIG. 2. The tracheal ends of the webs are cut back at an oblique angle as indicated at 8.

As can be seen from FIG. 3, which shows the sampler device in the assembled position, the tracheal end of the passage 6 in the tubular member 4 projects from the oblique end 3 of the chest tube 1. This tracheal end of the passage 6 is normally closed by a thin membrane (not shown) which is ruptured as a sampling catheter 9 is passed down the passage to project from the end of the passage. The chest tube is slightly curved for ease of insertion into the trachea.

In use, the chest tube 1 is inserted into the mouth or the nose of a patient to be examined, through the pharynx and upper respiratory tract, down into the trachea. Alternatively, the tube 1 may form a tracheostomy tube which is inserted into an ostium cut in the tracheal wall. The tubular member is next inserted into the tube 1 until its movement is limited by the rib 7a engaging the closed end 2a of the groove and then the sampling catheter 9 is inserted through the passage and membrane to extract a sample from the lower respiratory tract or trachea.

Referring now to the embodiment of FIGS. 4 and 5, parts of the sampler device corresponding to the embodiment of FIGS. 1 to 3 have the same reference numerals. Thus, the device comprises a flexible chest tube or Magill tube 1 made of a plastics material, but having a non-grooved internal wall. As previously, the tubular member 4 is made of a flexible plastics material and comprises a central cylindrical portion 5 defining a passage 6. In this embodiment three radially outwardly projecting webs 10 are provided which extend longitudinally over the forward end of the tubular member and which taper towards their ends. These webs engage the inner wall of the tube 1 to maintain the passage 6 spaced therefrom. An apertured stop member 11, which may be of oval or annular form in plan, is a frictional fit on the plain outer surface of the cylindrical portion 5 of the tubular member 4 and abuts against the outer end of the chest tube as the tubular member is inserted therein. Thus, this stop can be adjusted to position the forward end of the tubular member 4 relative to the forward end of the chest tube 1. The sampling catheter 9 is shown positioned within the tubular member 4 and the catheter is also provided with a stop member 12, similar to the stop member 11 and which is a frictional fit on the catheter 9. The stop member 12 is adjusted on the catheter so that the forward end of the catheter takes up the desired position in the trachea when the stop member 12 abuts against the outer end of the tubular member 4.

By means of the sampler device according to this invention, it is possible to take samples from the lower respiratory tract with the minimum risk of contamination from the pharynx, mouth and upper respiratory tract, whereby the tracheo-bronchial samples obtained through the catheter will virtually exclusively contain the infective germs and enable the cause of disease in the tracheal region to be precisely determined. This result is achieved by reason of the fact that the tubular member 4 and the sampling catheter 9 are maintained sterile in a package or packages until required for use, and since the passage 6 which receives the sampling catheter is spaced away from chest tube, the catheter does not become contaminated by germs on the wall of the chest tube which are picked up as the latter is inserted into the patient. Thus, the aseptic passage of the catheter into the trachea is ensured. Moreover, where a plastics membrane is provided over the tracheal end of the passage, this prevents the catheter from sliding and becoming contaminated until this membrane is broken by the catheter itself, which is only brought about when the device is in position to obtain a sample from the trachea. Where a stop member is provided on the sampling catheter, this can be adjusted to ensure accurate positioning of the inner end of the catheter in the desired region of the trachea, whilst the stop member on the tubular member prevents the latter sliding too far into the tracheal region.

The procedure of use is very easy with a patient under a respirator for daily sampling. It is more difficult to sample in an alert patient. The operator should then choose the right timing when the reflex cough due to the insertion of the chest tube has stopped.

Whilst a particular embodiment has been described, it will be understood that various modifications may be made without departing from the scope of this invention. Thus, the tubular member may be provided with a different number of webs. Alternatively, other means may be provided for holding the passage in the tubular member spaced from the wall of the chest tube, e.g. by providing a series of separate projections on the tubular member. It will be clearly understood that the components of the sampler device are made of suitable dimensions for the particular application envisaged, depending on the size of the patient and the method of insertion into the trachea.

I claim:

1. A tracheo-bronchial sampler device comprising:
   an outer chest tube capable of insertion into the trachea of a patient;
   a tubular member insertable in said chest tube and defining a passage through which a sampling catheter can be passed into the trachea;
   a plurality of longitudinal outwardly projecting webs on said tubular member, which are engageable with the inner walls of the chest tube and serve to hold the passage in the tubular member spaced away from the inner wall of the chest tube;
   and stop means for preventing the insertion of the tubular member through the chest tube beyond a predetermined point.

2. A sampler device as claimed in claim 1, wherein the webs extend only part of the way along the tubular member.

3. A sampler device as claimed in claim 1, wherein the leading or tracheal ends of the webs are cut-back.

4. A sampler device as claimed in claim 1, wherein the chest tube is provided with a longitudinal groove in its inner wall which slidably receives the outer edge of one of the webs as the tubular member is passed into the chest tube, the tracheal end of the groove being closed to define a stop which is engaged by the web to limit the movement of the tubular member into the chest tube.

* * * * *